United States Patent [19]

Chambers et al.

[11] Patent Number: 6,020,502

[45] Date of Patent: Feb. 1, 2000

[54] PREPARATION OF FLUORINATED DICARBONYLS

[75] Inventors: Richard D. Chambers; John Hutchinson, both of Durham; Martin P. Greenhall, Preston; John S. Moilliet, Preston; Julie Thomson, Preston, all of United Kingdom

[73] Assignee: BNFL Fluorochemicals Ltd., Salwick, United Kingdom

[21] Appl. No.: 08/704,546

[22] PCT Filed: Nov. 18, 1994

[86] PCT No.: PCT/GB94/02547

§ 371 Date: Feb. 21, 1997

§ 102(e) Date: Feb. 21, 1997

[87] PCT Pub. No.: WO95/14646

PCT Pub. Date: Jun. 1, 1995

[30] Foreign Application Priority Data

Nov. 20, 1993 [GB] United Kingdom .................. 9323919

Feb. 18, 1994 [GB] United Kingdom .................. 9403125

[51] Int. Cl.[7] .......................... C07D 307/58; C07C 67/30; C07C 45/65

[52] U.S. Cl. .............................. 549/322; 549/291; 560/51; 560/122; 560/125; 560/174; 560/178; 568/316; 568/348; 568/393

[58] Field of Search ............................... 560/51, 122, 125, 560/174, 178; 568/316, 348, 393; 549/322

[56] References Cited

U.S. PATENT DOCUMENTS 5,569,778  10/1996  Umemoto et al. ...................... 560/121

*Primary Examiner*—Bernard Dentz
*Attorney, Agent, or Firm*—Sheridan Ross P.C.

[57] ABSTRACT

A method for the fluorination of 1,3-diketones and 1,3-ketoesters is disclosed.

10 Claims, No Drawings

PREPARATION OF FLUORINATED DICARBONYLS

This application is a 371 of PCT/GB94/02547 filed Nov. 18, 1994.

FIELD OF THE INVENTION

The present invention relates to the preparation of dicarbonyls, in particular dicarbonyl compounds which are 2-fluoro- and 2,2-difluoro-1,3-diketones and -ketoesters.

BACKGROUND OF THE INVENTION

The use of elemental fluorine for the site specific fluorination of aliphatic compounds is rarely satisfactory due to the high reactivity of the element which leads to unspecific multiple substitution, carbon-carbon bond cleavage and oxidation. Because of the growing importance of fluorinated organic compounds in applications such as in biochemical systems, (Ref 1: R Filler, Y Kobayashi (editors); Biomedical Aspects of Fluorine Chemistry; Elsevier Biomedicinal Press, New York, 1982), (Ref 2: J T Welch; Tetrahedron, 1987, 43, (14), 3123) in recent years considerable effort has gone into finding ways of introducing fluorine into specific sites within molecules to provide building blocks for the preparation of biologically active compounds which have more complex structures. In this context, the replacement of the 2 hydrogen in 1,3-diketones and 1,3-ketoesters is just one transformation that has aroused much interest since the mono- and/or di-fluorinated products can be useful intermediates in the preparation of bio-active molecules. This transformation has been carried out either by treating the 1,3-diketone or 1,3-ketoester or their metal enolates with one of several "electrophilic fluorinating agents" that have been developed recently. For example, 1,3-diketones and 1,3-ketoesters have been treated with acetyl hypofluorite (Ref 3: S Rozen and O Lerman; J. Org. Chem., 1983, 48, 724), N-fluoro-pyridinium salts with or without a Lewis Acid catalyst (Ref 4: T Umemoto et al; J Amer. Chem. Soc., 1990, 112, 8563), xenon difluoride (Ref 5: B Zajc and M Zupan; J Chem Soc., Chem Commun, 1980, 759), lamellar $C_{19}XeF_6$ (Ref 6: H B Kagan, S S Yemul and R Setton; Tetrahedron Letts., 1980, 21, 277), and N-fluorobis[(perfluoroalkyl) sulphonyl]imides (Ref 7: G Resnati and D D Desmarteau; J Org. Chem., 1992, 57, 4281) (Ref 8: Z Xu, D D Desmarteau and Y Gotoh; J Fluorine Chem., 1992, 58, 71), (Ref 9: G Resnatti and D D Desmarteau; J. Org. Chem., 1991 56, 4925), (Ref 10 Z Xu, D D Desmarteau and Y Gotoh; J Chem Soc; Chem. Commun; 1991, 179) and their metal enolates have been treated with acetyl hypofluorite (Ref 3), N-fluoro-pyridinium salts (Ref 4).

Thus, although the treatment of 1,3-diketones and 1,3-ketoesters with electrophilic fluorinating agents can sometimes give high yields of the required mono- or di-fluorinated products, some of these reagents decompose fairly quickly, and the compounds from which they are made are often expensive or difficult to obtain.

SUMMARY OF THE INVENTION

According to the present invention there is provided a method for the production of 1,3-dicarbonyls of formula (1), (2), (3) or (4) as follows:

which comprises converting the corresponding compound of formula (5), (6), (7) or (8) as follows:

into compounds of formula (1), (2), (3) or (4) by reaction with elemental fluorine, wherein $R_1$ is selected from alkyl, substituted alkyl, cycloalkyl, aryl, substituted aryl and acetoxy, $R_2$ is selected from hydrogen, halogen, nitro, cyano, alkyl, cycoloalkyl, acetoxy and aryl substituted alkyl, acetoxy, aryl and substituted aryl, and $R_3$ is selected from alkyl, substituted alkyl, oxyalkyl and substituted oxyalkyl, $R_4$ and $R_5$ are hydrogen or alkyl n is an integer in the inclusive range 1 to 8 and the structures represented by formula (2), (3), (4), (6), (7) and (8) are cyclic, the process being carried out by passing fluorine gas into a solution of the appropriate compound of formula (5), (6), (7) or (8) in a substantially inert solvent comprising an acid such as formic acid of a mixture of neutral and acid solvents.

Where any one of the groups $R_1$, $R_2$ and $R_3$ is an alkyl, cycloalkyl or aryl group the group may include one or more optional substituents or hetero atoms.

Where $R_2$ in formula (5) is hydrogen, $R_2$ in formula (1) may be fluorine so that the product has formula (9) as follows:

Where $R_2$ in formula (7) is hydrogen, $R_2$ in formula (3) may be fluorine so that the product has the formula (10) as follows:

Fluorine itself has been rarely used for the conversion of 1,3-diketones or 1,3-ketoesters or their derivatives into the corresponding 2-fluorocompounds in the prior art. However, trimethyl silyl ethers of 1,3-diketones and 1,3-ketoesters have been converted by reaction with fluorine into the corresponding 2-fluoro-1,3-diketones and 2-fluoro-1,3-ketoesters in good yields but only at low (−78° C.) temperature and in a solvent (CFCl$_3$) which is to be phased out under the terms of the Montreal Protocol (Ref 11: S T Purrington, C L Bumgardner, N V Lazaridis and P Singh; J. Org. Chem., 1987, 52, 4307).

Surprisingly, we have now found that fluorine itself can be used to convert 1,3-diketones and 1,3-ketoesters into the corresponding 2-fluoro or 2,2-difluoro compounds in high yield and without the above disadvantages and this beneficially allows 1,3-diketones and 1,3-ketoesters of commercial value to be produced by a relatively simple and convenient route.

Desirably, the solvent overall is acidic ie pH≦7. We have found that use of formic acid optionally together with trifluoro acetic acid is especially preferred. In particular, formic acid forming from 70 to 90 percent by volume in a mixture wiyh triflouro acetic acid is particularly suitable. This gives a cleaner reaction than use of acetic acid plus sodium acetate in an essentially basic medium as used in the prior art. Such a medium produces fluorination via the hypofluorite rather than fluorine itself directly.

The reaction may be carried out in a vessel in which the solution is present or alternatively a flowing stream of the solution may be contacted with a gaseous flow of fluorine in countercurrent fashion.

The reaction of the process may be carried out at a temperature in the range −60° C. to +150° C. although a temperature of from −20° C. to +50° C. is preferred.

The fluorine gas is preferably diluted before use by mixing with an inert gas such as nitrogen or helium. The concentration of fluorine in inert gas is preferably from 1 percent to 50 percent by volume, preferably from 2 percent to 25 percent by volume, especially 5 percent to 15 percent by volume.

The ratio of fluorine to compound of formula (5), (6), (7) or (8) may be varied within wide limits although it is preferred that the molar ratio is in the range 0.5 to 4.0:1, especially 1.1 to 2.5:1 (fluorine:organic compound).

When fluorination is complete the fluorinated product in the process according to the present invention may be isolated by purging the reaction mixture with inert gas to remove any residual fluorine gas and hydrogen fluoride followed by dilution with excess water or aqueous solution and extraction into a suitable solvent followed by distillation.

Thus the present process according to the present invention provides an inexpensive and convenient synthetic route to 2-fluoro- and 2,2-difluoro-1,3-diketones and -1,3-ketoesters.

DETAILED DESCRIPTION OF THE INVENTION

Embodiments of the present invention will now be described by way of example only with reference to the following Examples.

EXAMPLE 1

Fluorination of Ethyl 2-cyclohexanone carboxylate

Through a stirred solution of ethyl 2-cyclohexanone carboxylate (4.25 gm., 0.025 m) in formic acid (50 ml) was bubbled fluorine (0.05 m), diluted with nitrogen to 10% fluorine, over 2 hours. The internal temperature was maintained in the range 4–8° C. When the reaction was complete, the vessel was purged with nitrogen and the contents were poured into water and extracted with dichloromethane. The solvent was removed from the dried (MgSO$_4$) extracts to yield ethyl 2-fluoro-2-cyclohexanone carboxylate, identified by its retention time which was coincident with that of an authentic sample, its NMR spectra [$^{19}$F(CDCl$_3$) $\delta_F$=−161.24 ppm (t) J$_{HF}$=16.4 Hz.], and Mass Spectrum (EI) [188, (M$^+$)]. Two small peaks in the gas chromatogram with longer retention times that the main product were recognised as 1) starting material, and 2) a compound with a molecular mass of 206 which corresponds to a molecular formula of C$_9$H$_{12}$F$_2$O$_3$. Conversion from ethyl 2-cyclohexanone carboxylate, 95%; Yield, 90%.

EXAMPLE 2

Fluorination of Ethyl-2-cyclohexanone carboxylate

This example was carried out in a similar manner to that described in Example 1, except that the solvent was acetonitrile and the temperature was maintained at about −10° C. Work up gave ethyl 2-fluoro-2-cyclohexanone carboxylate in 70% yield and C$_9$H$_{12}$F$_2$O$_3$ in a ca.8% yield. The conversion was ca.90%.

EXAMPLE 3

Fluorination of Ethyl-2-cyclohexanone carboxylate

This example was carried out as in Example 1 except that solvent consisted of a mixture of formic acid (40 ml) and water (10 ml), and the reaction temperature was maintained at ca.10° C. The yield of ethyl 2-cyclohexanone carboxylate was 95% and the conversion was 90%.

EXAMPLE 4

Fluorination of Ethyl-2-oxocyclopentane carboxylate

Ethyl-2-oxocyclopentane carboxylate (3.9 gm 0.025 m) was fluorinated in a similar manner to that described in Example 1. Work up gave ethyl-2-fluoro-2-oxocyclopentane carboxylate [NMR(CDCl$_3$); $^{19}$F, $\delta_F$=−164.6 ppm (t) J$_{HF}$=21.0 Hz. MS (EI); M$^+$ 174]. Yield 56%. Also recognised in the reaction mixture was cyclopentanone [M.S. (EI); 84(M$^+$)], unreacted starting material, and diethyl adipate [M.S. (CI); 203 (M+1)$^+$]. Conversion 80%.

EXAMPLE 5

Fluorination of Ethyl acetoacetate

The fluorination of ethyl acetoacetate (3.25 gm, 0.025 m) was carried out in a similar manner to that described in Example 1 except that the fluorine (0.05 m) was passed through the reaction mixture over a period of 4 hours and the reaction temperature was maintained at ca. 10° C. Work up gave ethyl 2-fluoroacetoacetate [NMR(CDCl$_3$); $^{19}$F, $\delta_F$=−193.70 ppm (dq) J$_{HF}$=49.4 Hz, J$_{HF}$=12.1 Hz M.S. (EI); 148 (M$^+$)]. A small singlet in the reaction product at −114.7 ppm was attributed to ethyl 2,2-difluoroacetoacetate. A small doublet at −204.5 ppm (J$_{HF}$=43.0 Hz) and triplet of equal intensity at −235.8 ppm (J$_{HF}$=45.3 Hz) were attributed to ethyl 2-fluoro-2-(fluoroacetyl)acetate. Total Yield, >90%. Conversion, 90%.

EXAMPLE 6

Fluorination of Ethyl 2-chloroacetoacetate

The fluorination of ethyl 2-chloroacetoacetate (4.1 gm, 0.025 m) was carried out in a similar manner to that described in Example 1 except that the temperature was maintained in the range 10–15° C. Work up gave ethyl 2-chloro-2-fluoroacetate [NMR (CDCl$_3$); $^1$H, $\delta_H$=4.39 ppm (q, J$_{HH}$=7.3 Hz, CH$_3$CH$_2$), 2.46 ppm (d, J$_{HF}$=2.6 Hz, CH$_3$CO), 1.36 ppm (t, J$_{HH}$=7.1 Hz, CH$_3$CH$_2$); $^{19}$F, $\delta_F$=–123.5 ppm (J$_{HF}$=2.4 Hz): MS (EI); 183 (M+1)]. A small broad singlet at –127.6 ppm and triplet of doublets at –234.7 ppm (J$_{HF}$=46.3 Hz, J$_{FF}$=1.9 Hz) were attributed to ethyl 2-chloro-2-fluoro-2-(fluoroacetyl)acetate. Conversion of starting material to product was ca. 15% and the yield was ca. 90%.

EXAMPLE 7

Fluorination of ethyl 2-chloroacetoacetate

This experiment was carried out in a manner similar to that in Example 6 except that 1.9 gm of sodium formate was added to the reaction mixture. This has the effect of increasing the conversion to 45%. The yield and nature of the product were similar to those in Example 6.

EXAMPLE 8

Fluorination of ethyl 2-methylacetoacetate

The fluorination of ethyl 2-methylacetoacetate (3.6 gm, 0.025 m) was carried out in a manner similar to that described in Example 6. Work up gave Ethyl 2-fluoro-2-methylacetoacetate [NMR (CDCl$_3$); $^{19}$F, $\delta_F$=–157.7 ppm (q-q, J$_{HF}$=22.1 Hz, J$_{HH}$=4.5 Hz): MS (EI); 163(M+1)]. A small quartet of multiplets at –166.6 ppm (J$_{HF}$=23.2 Hz) and triplet of doublets at –236.0 ppm (J$_{HF}$=46.7 Hz, J$_{FF}$=3.7 Hz) in the reaction product were attributed to ethyl 2-fluoro-2-(fluoroacetyl)-2-methyl acetate. Conversion of starting material to product was ca. 25% and the yield was ca. 90%.

EXAMPLE 9

Fluorination of 2-Acetyl butyrolactone

The fluorination of 2-Acetyl butyrolactone (3.2 gm, 0.025 m) was carried out in a manner similar to that described in Example 6. Work up gave 2-fluoro-2-acetyl butyrolactone (nc) [NMR (CDCl$_3$); $^1$H, $\delta_H$=4.5 ppm (m), 2H; 2.87 ppm (m), 1H; 2.55 ppm (m)1H; 2.47 ppm (d), J$_{HF}$=5.0 Hz, 3H; $^{19}$F, $\delta_F$=–163.4 ppm (ddqd), J=11.8, 11.8, 4.9, and 1.5 Hz]. Accurate mass measurement:—Found (CI, methane), 147.0442; C$_6$H$_8$O$_3$F requires 147.0457]. A small multiplet at –173.8 ppm and triplet of doublets at –237.9 ppm (J$_{triplet}$=46.3 Hz, J$_{doublet}$=6.8 Hz) in the reaction product were attributed to 2-fluoro-2-(fluoroacetyl)butyrolactone. The conversion was ca. 70% and the yield was ca. 85%.

EXAMPLE 10

Fluorination of Ethyl 4-chloroacetoacetate

The fluorination of ethyl 4-chloroacetoacetate (4.1 gm, 0.025 m) was carried out in a manner similar to that described in Example 6. Work up gave ethyl 2-fluoro-4-chloroacetoacetate(nc) [NMR (CDCl$_3$); $^{19}$F, $\delta_F$=198.8 ppm (td), J$_{HF}$=48.5 Hz and J$_{HF}$=3.3 Hz. Accurate mass measurement:—Found (CI, methane), 183.0178; C$_6$H$_9$O$_3$ClF requires 183.0224].

EXAMPLE 11

Fluorination of 2,4-Pentanedione

Through a stirred solution of 2,4-pentanedione (2.5 gm, 0.025 m) in formic acid (50 ml) was bubbled fluorine (0.05 m), diluted with nitrogen to 10% fluorine, over 2 hours. The internal temperature was maintained in the range 10–15° C. When the reaction was complete, the vessel was purged with nitrogen and the contents were poured into water and extrated with dichloromethane. The solvent was distilled from the dried MgSO$_4$ extracts to yield 3-fluoro-2,4-pentanedione [NMR(CDCl$_3$); $^1$H, $\delta_H$=5.25 ppm (d, J$_{HF}$=50.0 Hz, CHF), 2.31 ppm (m, keto 2×CH$_3$), 2.18 ppm (m, enol 2×CH$_3$); $^{19}$F, $\delta_F$=–192.0 ppm (dm, J$_{HF}$=49.2 Hz, keto ca, 6.5 parts) and –173.7 ppm (s, enol ca. 1 part). MS (EI); 118, (M$^+$)]. Also detected in the reaction product was a small singlet at –115.4 ppm which was attributed to 3,3-difluoro-2,4-pentanedione [MS (EI); 136(M$^+$), 94(M$^+$—CH$_2$CO)], and a doublet at –204.0 ppm (J$_{HF}$=42.4 Hz) and triplet of doublets at –236.6 ppm (J$_{HF}$=46.2 Hz, J$_{FF}$=2.8 Hz) which were attributed to 1,3-difluoro-2,4-pentanedione [MS (EI); 136(M$^+$), 103(M$^+$—CH$_2$F)]. Conversion, 90%; Total Yield, 85%.

EXAMPLE 12

Fluorination of 2,4-Pentanedione

In a similar reaction to that described in Example 11, fluorine (0.28 m) was passed through a solution of 2,4-pentanedione (0.113 m) in formic acid (225 ml) over a period of 18 hours. The reaction product was mainly 3-fluoro-2,4-pentanedione, with much smaller amounts of 3,3-difluoro-2,4-pentanedione and 1,3-difluoro-2,4-pentanedione. Conversion, 100%.

EXAMPLE 13

Fluorination of 3-Methyl-2,4-pentanedione

In a similar reaction to that described in Example 11, fluorine (0.05 m) was passed through a solution of 3-methyl-2,4-pentanedione (0.025 m) in formic acid (50 ml). The main product was identified as 3-fluoro-3-methyl-2,4-pentanedione [NMR(CDCl$_3$); $^1$H, $\delta_H$=1.6 ppm (3H, d, J$_{HF}$=22 Hz, CFCH$_3$), 2.3 ppm(6H, d, CH$_3$), J$_{HF}$=3.2 Hz; $^{19}$F, $\delta_F$=–158.0 ppm (q, J=22 Hz). MS (EI); 133(M$^+$+1), 90(M$^+$—CH$_2$CO), 43(CH$_3$CO)]. Also produced in the reaction was ca. 10% of 1,3-difluoro-3-methyl-2,4-pentanedione [NMR(CDCl$_3$); $^{19}$F, $\delta_F$=166.1 ppm (q, J$_{HF}$=23 Hz), –235.3 ppm (t, J$_{HF}$=46.5 Hz). MS (EI); 150(M$^+$), 61(CH$_2$FCO), 43(CH$_3$CO)]. Conversion, 90%; Yield (monoF), 80%.

EXAMPLE 14

Fluorination of 3-Chloro-2,4-pentanedione

In a similar way to that described in Example 11, fluorine (0.05 m) was passed through a solution of 3-chloro-2,4-pentanedione (0.025 m) in formic acid (50 ml) over a period of 2 hours. The product was identified as 3-chloro-3-fluoro-2,4-pentanedione [NMR(CDCl$_3$); $^1$H, $\delta_H$= 2.4 ppm (d, J$_{HF}$=3 Hz); $^{19}$F, $\delta_F$=–126.2 ppm (septet, J$_{HF}$=3 Hz). MS (EI); 152 (and 154)(M$^+$), 117 (M$^+$—Cl), 110 (M$^+$—COCH$_2$)]. A singlet with $\delta_F$–129.3 ppm and triplet at $\delta_F$=–233.8 ppm of equal intensity in the $^{19}$F NMR of the product was attributed to 1,3-difluoro-3-chloro-2,4-pentanedione. Conversion, 85%; Yield 70%.

EXAMPLE 15

Fluorination of 2-Acetylcylohexanone

In a similar way to that described in Example 11, fluorine (0.05 m) was passed through a solution of 2-acetylcyclohexanone (0.025) in 50 ml formic acid over a period of 2 hours. The main product was identified as 2-acetyl-2-fluorocyclohexanone [NMR(CDCl$_3$); $^{19}$F, $\delta_F$=−157.8 ppm. MS (EI); 158(M$^+$), 116 (M$^+$—COCH$_2$)]. Also detected in the reaction product was 2-(fluoroacetyl)-2-fluorocyclohexanone [NMR(CDCl$_3$); $^{19}$F, $\delta_F$=−168.8 ppm (m) and −236.9 ppm (td), J$_{HF}$=46.8 ppm, J$_{FF}$=7.3 Hz MS (EI); 176(M$^+$)]. Conversion, 95%; Yield (monoF), 80%; (diF), 10%.

EXAMPLE 16

Fluorination of Benzoyl acetone

In a similar way to that described in Example 11, fluorine (0.05 m) was passed through a solution of benzoyl acetone (0.025 m) in 50 ml formic acid over a period of 2 hours. The main product was identified by its NMR(CDCl$_3$) [$^{19}$F, $\delta_F$=−190.1 ppm (d), J$_{HF}$=50.0 H\(keto) and −170.5 ppm (s)(enol)] and mass spectra [(EI) 180(M$^+$), 105(C$_6$H$_5$CO), 77(C$_6$H$_5$)] as 1-phenyl-3-fluoro-2,4-pentanedione. Also formed were compounds in which fluorine had attached the aromatic ring.

While various embodiments of the present invention have been described in detail, it is apparent that modifications and adaptations of those embodiments will occur to those skilled in the art. It is to be expressly understood that such modifications and adaptations are within the scope of the present invention, as set forth in the following claims.

What is claim is:

1. A method for the production of 1,3-diketones and 1,3-ketoesters having a formula selected from the group consisting of (1), (2) and (3) as follows:

(1)

(2)

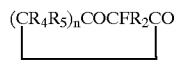
(3)

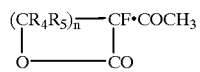
(4)

which comprises converting a corresponding compound having a formula selected from the group consisting of (5), (6), (7) and (8) as follows:

(5)

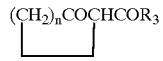
(6)

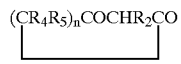
(7)

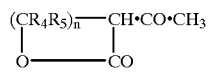
(8)

into compounds of formula (1), (2), (3) or (4) by reaction with elemental fluorine, wherein R$_1$ is selected from the group consisting of alkyl, substituted alkyl, cycloalkyl, aryl, substituted aryl and acetoxy, R$_2$ is selected from the group consisting of hydrogen, halogen, nitro, cyano, alkyl, cycloalkyl, acetoxy and aryl substituted alkyl, acetoxy, aryl and substituted aryl, and R$_3$ is selected from the group consisting of alkyl, substituted alkyl, oxyalkyl and substituted oxyalkyl, R$_4$ and R$_5$ are hydrogen or alkyl, n is an integer in the inclusive range of 1 to 8 and the structures represented by formula (2), (3), (4), (6), (7) and (8) are cyclic, the process being carried out by passing fluorine gas into a solution of the appropriate compound of formula (5), (6), (7) or (8) in a substantially inert solvent comprising an acid having a pH<7 wherein said solvent comprises formic acid.

2. A method as in claim 1, wherein R$_2$ in formula (5) or formula (7) is hydrogen, R$_2$ in formula (1) or formula (3) is fluorine and the product has a formula selected from the group consisting of (9) and (10) as follows:

3. A method as in claim 1, wherein the fluorine gas is diluted before use by mixing with an inert gas.

4. A method as in claim 3 wherein the inert gas comprises nitrogen or helium and forms from 1 percent to 50 percent by volume of the gas mixture.

5. A method as in claim 3 in which a flow of said solution is contacted with a gaseous flow of fluorine in a mixture with an inert gas in countercurrent fashion.

6. A method as in claim 1 wherein the molar ratio of fluorine to compound of formula (5), (6), (7) or (8) is in the range of 0.5:1 to 4.0:1.

7. A method as set forth in claim 1, wherein said process is performed substantially in the absence of any base or acid additives other than said formic acid.

8. A method as set forth in claim 7, wherein said process is performed substantially in the absence of any mineral acid additives.

9. A method according to claim 7, wherein said process is performed substantially in the absence of additional water.

10. A method for the production of 1,3-diketones and 1,3-ketoesters having a formula selected from the group consisting of (1), (2) and (3) as follows:

(1)

(2)

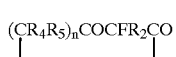
(3)

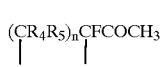
(4)

which comprises converting a corresponding compound having a formula selected from the group consisting of (5), (6), (7) and (8) as follows:

  (5)

  (6)

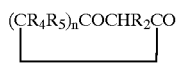  (7)

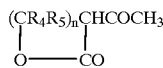  (8)

into compounds of formula (1), (2), (3) or (4) by reaction with elemental fluorine, wherein $R_1$ is selected from the group consisting of alkyl, substituted alkyl, cycloalkyl, aryl, substituted aryl and acetoxy, $R_2$ is selected from the group consisting of hydrogen, halogen, nitro, cyano, alkyl, cycloalkyl, acetoxy and aryl substituted alkyl, acetoxy, aryl and substituted aryl, and $R_3$ is selected from the group consisting of alkyl, substituted alkyl, oxyalkyl and substituted oxyalkyl, $R_4$ and $R_5$ are hydrogen or alkyl, n is an integer in the inclusive range of 1 to 8 and the structures represented by formula (2), (3), (4), (6), (7) and (8) are cyclic, the process being carried out by passing fluorine gas into a solution of the appropriate compound of formula (5), (6), (7) or (8) in a substantially inert solvent comprising an acid having a pH<7 wherein said solvent consists essentially of formic acid.

* * * * *